United States Patent [19]

Smets

[11] 4,422,369

[45] Dec. 27, 1983

[54] METHOD AND APPARATUS FOR STERILIZING A GAS, AND DEVICE FOR CONDITIONING AND PROTECTING A ZONE FROM A SPACE

[75] Inventor: Willy Smets, Uccle, Belgium

[73] Assignees: E.N.I. Electrische Nijverheidsinstallaties; E.N.I. l'Electro navale et industrielle, both of Aartselaar, Belgium

[21] Appl. No.: 430,887

[22] Filed: Sep. 30, 1982

Related U.S. Application Data

[63] Continuation of Ser. No. 149,713, May 14, 1980, abandoned.

[30] Foreign Application Priority Data

May 18, 1979 [LU] Luxembourg ............................ 81292

[51] Int. Cl.³ .................... F24F 9/00; A61G 13/00
[52] U.S. Cl. .................... 98/36; 55/DIG. 29; 128/1 R
[58] Field of Search ............ 98/36; 55/DIG. 29; 128/1 R, 1 B, 132 R, 132 D

[56] References Cited

U.S. PATENT DOCUMENTS

| | | | |
|---|---|---|---|
| 3,221,632 | 12/1965 | Copp | 98/36 X |
| 3,820,536 | 6/1974 | Anspach, Jr. et al. | 55/DIG. 29 X |
| 3,923,482 | 12/1975 | Knab et al. | 98/36 X |
| 4,140,105 | 2/1979 | Duvlis | 98/36 X |

FOREIGN PATENT DOCUMENTS

| | | |
|---|---|---|
| 1048005 | 12/1958 | Fed. Rep. of Germany .......... 98/36 |
| 1120104 | 12/1961 | Fed. Rep. of Germany .......... 98/36 |
| 2343015 | 2/1975 | Fed. Rep. of Germany . |
| 2512679 | 9/1976 | Fed. Rep. of Germany . |
| 2708641 | 8/1978 | Fed. Rep. of Germany . |
| 2736837 | 3/1979 | Fed. Rep. of Germany .......... 98/36 |
| 2118891 | 8/1972 | France . |
| 2141861 | 1/1973 | France . |
| 2252852 | 6/1975 | France . |
| 2293945 | 7/1976 | France . |
| 321792 | 5/1957 | Switzerland ........................... 98/36 |
| 904052 | 8/1962 | United Kingdom . |
| 1127793 | 9/1968 | United Kingdom . |
| 1180970 | 2/1970 | United Kingdom ................... 98/36 |
| 1190380 | 5/1970 | United Kingdom . |
| 1275569 | 5/1972 | United Kingdom . |
| 1295551 | 11/1972 | United Kingdom . |
| 1349717 | 4/1974 | United Kingdom . |
| 1531514 | 11/1978 | United Kingdom . |

OTHER PUBLICATIONS

Pfiffelmann et al., "L'air laminoire et les zones propres", *Produits et Problemes Pharmaceutiques*, vol. 28, No. 8, 9–1973, Societe de Productions Documentaires.

*Primary Examiner*—Harold Joyce
*Attorney, Agent, or Firm*—Wood, Dalton, Phillips, Mason & Rowe

[57] ABSTRACT

There is described a method for protecting and conditioning a zone, such as an operating field, from a space. Said zone is bounded relative to the environment on at least one side thereof, by a curtain which is comprised of a substantially laminar stream from an essentially sterile gas such as air, and within said zone is fed preferably substantially continuously, some essentially sterile conditioned gas, in such a location, with such a speed and along such a direction that said curtain will not be disturbed.

There is also described a device for the working of this method and a method for sterilizing a gas stream.

9 Claims, 7 Drawing Figures

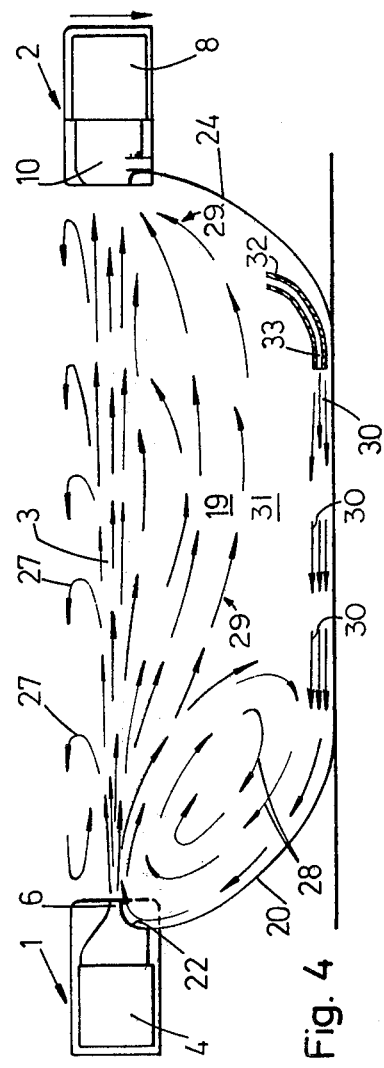
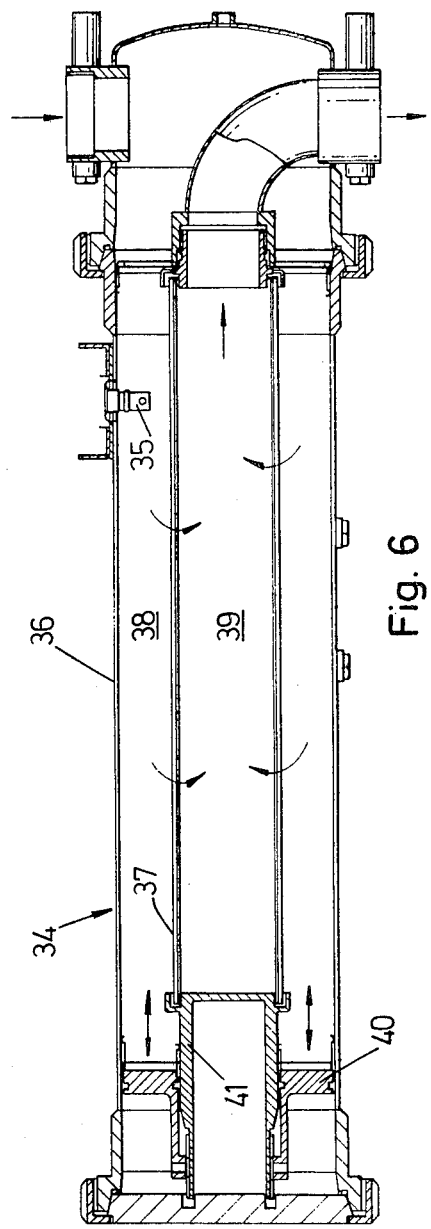

METHOD AND APPARATUS FOR STERILIZING A GAS, AND DEVICE FOR CONDITIONING AND PROTECTING A ZONE FROM A SPACE

This is a continuation of application Ser. No. 149,713 filed May 14, 1980 now abandoned.

This invention relates to a method for conditioning a determined zone from a space and for protecting said zone against contaminating agents entering from the outside, and protecting an operating field relative to the environment.

It is presently recognized that an increasing number of surgery operations require working with intricate protecting means to dispose of the danger of contaminating a patient during the operation, with the environment or the surgeon himself.

Some means used, such as operating bubbles for isolating the patient or diving-suits for isolating the surgeon, comprise a severe handicap and constraint for the surgeon during the operation.

A main object of the invention is to provide a method which allows obviating the drawbacks of the above-defined means and generating moreover in the very zone, a thoroughly conditioned medium, a so-called "micro-climate".

For this purpose according to the invention, the zone to be protected such as the operating field and the direct surroundings thereof is bounded relative to the environment on at least one side thereof, by a curtain which is comprised of a substantially laminar stream from an essentially sterile gas such as air, and within said zone is fed preferably substantially continuously, some essentially sterile conditioned gas, in such a location, with such a speed and along such a direction that said curtain will not be disturbed.

The invention also relates to a device for the working of the above method, notably a device for conditioning and protecting a determined zone from a space against contaminating agents from the outside, more particularly an operating field relative to the environment, which comprises at least one blowing manifold and one sucking manifold for gas arranged some distance away from one another while being so directed as to allow forming a gas curtain between both said manifolds.

Said device is characterized in that the blowing manifold is connected to the outlet from a gas-sterilizing apparatus, while the sucking manifold is connected to said apparatus inlet and a duct for feeding conditioned gas also connected to said sterilizing outlet, opens inside said zone.

The invention further pertains to a method for sterilizing a gas stream, such as an air stream, which is notably intended to protect a determined zone from a space against contaminating agents from the outside.

Said method is characterized in that said gas stream to be sterilized is passed through a filtering medium allowing to retain micro-organisms, and said filtering medium is subjected to an in-depth sterilizing treatment to destroy the micro-organisms which have been retained by said filtering medium.

Advantageously, said filtering medium and the gas stream are continuously subjected to a sterilizing treatment during the passage of said stream through said medium.

Finally the invention relates to a sterilizing apparatus for the working of said method.

Said apparatus comprises at least one microfilter and sterilizing means mounted upstream or in the location of the micro-filter, said means causing an in-depth sterilizing in the micro-filter filtering medium.

Other details and features of the invention will stand out from the following description, given by way of non limitative example and with reference to the accompanying drawings, in which:

FIG. 4 shows diagrammatically the dynamic action of air in a vertical and lengthwise cross-section of a protected zone according to the invention.

FIG. 6 is a lengthwise section on a larger scale, through part of the apparatus as shown in FIG. 5.

In the various figures, the same reference numerals pertain to identical or similar elements.

The method and device according to the invention are generally designed to protect a determined zone from a space against contaminating agents which might originate from the outside, and to condition said zone as regards the temperature and hygroscopy thereof.

Figure 1:
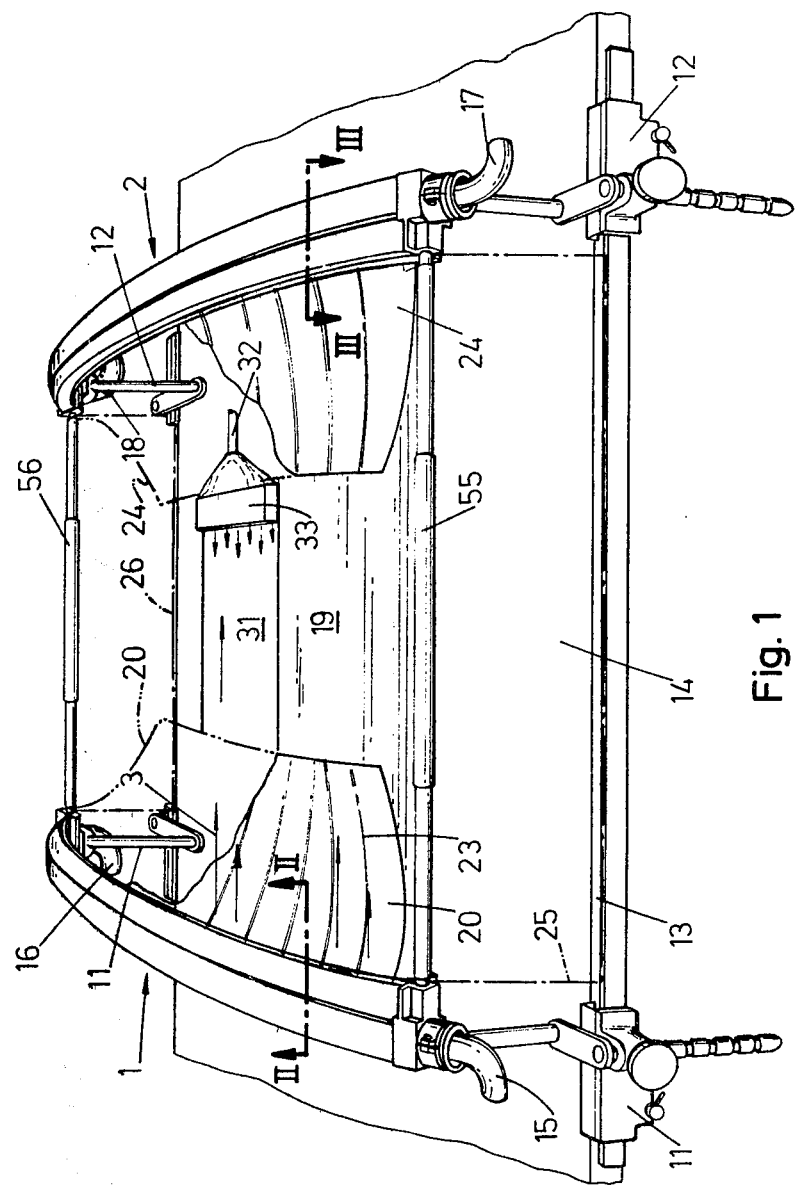
FIG. 1 is a diagrammatic perspective view from a particular embodiment of a device for protecting an operating field.
Figure 2:
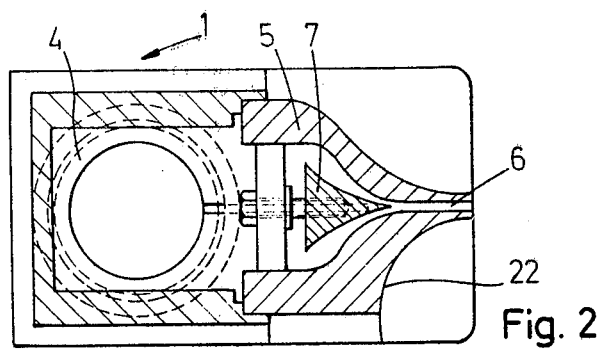
FIG. 2 is a section view along line II—II in FIG. 1.
Figure 3:
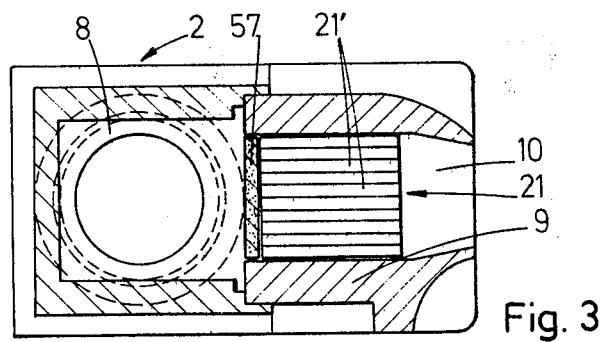
FIG. 3 is a section view along line III—III in FIG. 1.

However as the preferred use of said method and device comprises the conditioning and protecting of an operating field relative to the environment, the following description will be limited to such a specific use with reference to FIGS. 1 to 3.

The device for protecting an operating field as shown in said figures comprises a blowing manifold 1 for sterile air and a sucking manifold 2, both manifolds being shaped as an arc of circle and extending in vertical planes which are in substantially parallel relationship with one another.

Moreover said manifolds 1 and 2 are so directed towards one another as to allow obtaining a curtain 3 in the shape of part from a cylindrical wall and comprised of a substantially laminar stream from sterile air.

Said sterile air curtain comprises a barrier for the passage of contaminating agents which as they contact said curtain, are carried away thereby into the sucking manifold.

The blowing manifold 1 comprises a distributing chamber 4 in the shape of an arc of circle which extends over an angle in the range from 110° to 120°, open sidewise on the side of sucking manifold 2 and provided on said side with an outlet mouth 5. Said mouth is provided with a slot 6 that comprises the outlet from the blowing manifold.

In the inlet of slot 6 is engaged a relatively flexible adjusting needle 7 which allows varying the air throughput therethrough and adjusting uniformly the air distribution along blowing manifold 1.

The sucking manifold 2 has substantially the same shape as said manifold 1 and also comprises a distributing chamber 8 shaped as an arc of circle. Said chamber is open sidewise on the side of the blowing manifold, and it is provided all along said side with a mouth 9 having a slot 10. The slot width is much larger than the slot width of blowing manifold 1 to take into consideration on the one hand, the diverging air jet originating from said blowing manifold and on the other hand, the fact that part of the air from that zone to be protected proper has to be sucked by said manifold 2.

Moreover a distributing strip 21 with a honeycomb structure arranged over a porous support 57, is engaged inside slot 10 to form channels 21' set side by side in parallel relationship with the gas stream passing through said elemennt. Said channels also allow to retain inside slot 10 a substantially laminar flow with an uniform distribution.

The blowing manifold 1 and the sucking manifold 2 are mounted independently from one another through a fastener 11, 12 respectively, in guide rails 13 which extend along the lengthwise edges from an operating table 14 the protecting device is mounted on.

In each end of blowing manifold 1 ends a pipe 15, 16 respectively for feeding sterile air.

In the same way, sucked air discharge pipes 17 and 18 are connected to the ends of sucking manifold 2.

The fasteners 11 are mounted in an adjustable position in the rails 13 to allow varying the spacing between manifolds 1 and 2 and the relative position thereof on different types of operating tables 14.

The curtain 3 formed by the sterile air stream between manifolds 1 and 2 bounds the top side of the zone to be protected and conditioned. Said zone 19 is closed on the side of the blowing manifold by a baffle 20 with a concave shape on the side of zone 19.

The blowing manifold 1 is provided on the side of the zone 19 to be protected and from slot 6, with a curved wall 22 in the extension of which extends the baffle 20 having substantially the same curvature as said wall, to form therewith a substantially continuous concave surface.

To insure as complete as possible sealing by means of baffle 20, said baffle is made from a relatively tight fabric having associated therewith stiffening elements 23 which allow adapting the bottom baffle edge to a patient lying on operating table 14, below manifolds 1 and 2.

In a similar way, a similar baffle 24 is provided on the side of the sucking manifold.

Moreover, relatively flexible side barriers 25 and 26 which are adjustable to the patient shape to prevent also as far as possible sidewise entry of outside air to the operating field, hang from telescoping rods 55 and 56 which connect both manifolds 1 and 2.

In such a way there is obtained a closed enclosure the top wall of which is formed by curtain 3 and the side walls of which are formed by baffles 20 and 24 and flexible barriers 25 and 26.

Advantageously according to the invention, inside zone 19 is fed some essentially sterile conditioned gas, in such a location, with such a speed and along such a direction that said curtain 3 will not be disturbed.

Said gas is preferably fed inside zone 19 along a direction which is opposed to the direction of that gas stream forming curtain 3, on the side of sucking manifold 2 and substantially level with the operating field, that is on that side removed from the side bounded by curtain 3.

Said gas feeding location and speed are selected according to the speed of that gas forming curtain 3, in such a way as to neutralize in a determined part from said zone, notably about said operating field, disturbances in the gas flow caused by the gas stream forming the curtain, and thus to generate in said part a gas layer with a very slow flow speed, in such a way that said layer might be considered practically as being substantially unmoving or stationary.

FIG. 4 shows diagrammatically the dynamic action of the air inside zone 19. As shown in FIG. 4, that gas stream forming curtain 3 causes due to a friction phenomenon in that adjacent air layers, secondary gas streams.

The nature of said secondary streams differs according to whether they occur above the curtain-forming stream or below same.

Indeed it is generally noted that above the curtain uncontrolled vortexes are formed in the air layer contacting the curtain, as shown by arrows 27, according to the theory of the free jets in the presence of a boundary layer.

Such condition is completely different below the curtain in the zone to be protected, due to the presence of baffle 20, by analogy with restrained jets in the presence of re-circulating.

Indeed due to friction between that air stream forming the curtain and the adjacent layers from the zone to be protected, the secondary air stream thus obtained generates adjacent baffle 20, an underpressure which then causes a local re-circulating along the direction shown by arrows 28. Said re-circulating 28 then causes in turn together with that gas stream forming curtain 3, a gas stream through the zone to be protected proper, substantially along the direction of curtain 3 as shown by reference numeral 29.

It has been noted according to the invention that it is possible to retain a substantially unmoving air layer in a determined part from said zone by feeding thereto said gas amount along a direction opposed to the direction of that stream formed by curtain 3. Such gas feeding has been shown diagrammatically at 30 in FIG. 4.

The selection of the feeding location and speed for said gas amount is essentially dependent on the spacing between that zone part where said substantially unmoving gas layer from the stream forming curtain 3 is to be generated, as well as on the stream speed.

Said part of the zone to be protected where a substantially unmoving air layer is generated is shown in 31.

In spite of the air layer being substantially unmoving, it is however noticed that it is continuously renewed by the continuous feeding of said gas amount 30 and also due to said layer being licked by low-speed substantially laminar gas streams which regularly replace that gas film bounding layer 31 to carry same in the flow 28 towards sucking manifold 2. There is thus actually generated a quasi-unmoving gas layer in the location of the operating field.

Due to such dynamic action from the gas in zone 19, it is possible according to the invention, to generate in some pre-determined part thereof a micro-climate by feeding in a location with some well-determined direction and speed, a pre-conditioned gas volume.

Advantageously the gas amount fed is moist and preferably saturated with water-vapour or steam, also with a controlled temperature.

It is moreover noticed that good results are obtained as regards the stability of the micro-climate about the operating field, when curtain 3 lies at a distance from 10 to 30 cm and preferably from 10 to 15 cm, from the oprating field.

Moreover to insure said dynamic action of the gas inside the zone 19 to be protected and prevent the leakage of contaminating agents through curtain 3, the speed of that gas stream forming said curtain should not fall down below 2 m/sec. as it enters sucking manifold 2. For this reason a speed between 2 and 20 m/sec. is advantageously maintained for the gas stream between manifolds 1 and 2.

The stream thickness has a mean value lying between 0.2 and 5 cm, while the length and width thereof which vary of course according to the nature of the surgery operation, are repectively from 40 to 70 cm and from 20 to 60 cm.

As it appears from the above considerations as regards the dynamic action of the gases inside the zone to be protected according to the invention, besides substantially all of the gas originating from blowing manifold 1, some gas amount is sucked from the zone to be protected proper, such amount corresponding substantially to the gas amount fed thereto.

The gas sucked by manifold 2 is returned to a sterilizing apparatus which will be further described hereinafter and on the one hand the outlet from which is connected to blowing manifold 1 and to a gas-feeding pipe 32 opening inside zone 19 to be protected, and on the other hand the inlet to which communicates with sucking manifold 2, thus allowing to re-cycle to sterilizing at least for the larger part, that air used to form curtain 3.

Said pipe 32 comprises at least one flexible section to allow adjusting the position and the direction thereof inside zone 19.

Moreover said pipe 32 is advantageously provided with an outlet opening 33 in the shape of a flattened cone to allow feeding gas to zone 19 as a sheet with some width and a relatively low speed.

To allow adjusting the moistness of the gas amount fed through pipe 32 into zone 19 to be protected, a moistening and possibly cooling and heating device is built in the sterilizing apparatus.

The invention further relates to a specific method for sterilizing a gas stream, notably an air stream, which is for instance intended for conditioning and protecting a determined zone from a space against contaminating agents originating from the outside, such as an operating field.

According to said method, said gas or air stream is passed through a filtering medium allowing to retain micro-organisms and said filtering medium is subjected to an in-depth sterilizing treatment to destroy the micro-organisms which have been retained therein.

Said method will be further described with reference to FIGS. 5 to 7 which show two embodiments of the air-sterilizing apparatus according to the invention, as connected to a device of the type as shown in FIGS. 1 to 3 and described above.

Said apparatus essentially comprises a micro-filter 34 allowing to retain particles of 0.2 micron and preferably in the range of 0.01 micron, and sterilizing means arranged upstream or in the location of the micro-filter, said means being so designed as to cause an in-depth sterilizing of the filtering medium from said micro-filter.

Figure 5:
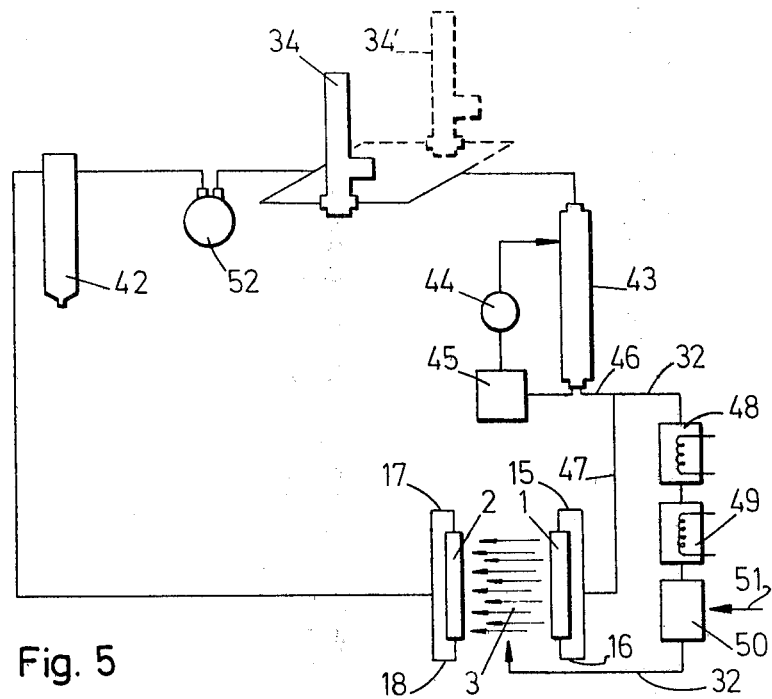
FIG. 5 is a block diagram of a sterilizing apparatus in a first embodiment of the invention.

In the embodiment as shown in FIGS. 5 and 6, said sterilizing means comprise a microwave sending aerial 35 which is mounted inside micro-filter 34.

Said micro-filter has been shown with more details in FIG. 6 and it is provided with a cylindrical casing 36 bouding an enclosure inside which is provided a cylindrical filtering wall 37 which forms said filtering medium proper. Said filtering wall divides the enclosure into two compartments 38 and 39.

The aerial 35 is mounted on wall 36 inside the compartment 38 that forms a cavity containing said filtering medium.

Said filtering wall 37 is advantageously comprised of at least two filtering layers with different porosity, the first layer actually forming a prefilter and being located on the side of compartment 38, the second layer having a finer structure, notably by being comprised of a micro-fiber fabric.

Said micro-filter is mainly characterized in that the length of compartment 38 is adjustable according to the wave length of the microwaves, by means of a ring-like piston 40 which is slidable some distance over a core 41. The relative position from said piston is so selected as to cause resonating of the microwaves inside said micro-filter 34.

There results therefrom a dielectric heating of the filtering wall proper to a temperature varying between 100° and 200° C. according to the flow rate, the moisture content of the air and the power of the magnetron, not shown, which generates the microwaves. On the other hand the air temperature does only increase by a few degrees (4° to 10° C.).

As shown in FIG. 5, said apparatus comprises besides said micro-filter 34, a prefilter 42 for stopping the particles with a size larger than 10 microns which might clog other parts from the apparatus.

Said micro-filter 34 is then followed by a cooler 43 with injection of water supplied through a metering pump 44 connected to a water tank 45 which recovers water from the cooler.

The sterilized air thus cooled to room temperature is fed through a pipe 46 for instance to a device for conditioning and protecting a zone 19 as described above.

Said piper 46 branches into a pipe 47 directly connected to blowing manifold 1 and a pipe 32 feeding part of the sterilized air to a conditioning unit comprising a heater 48, a cooler 49 and a moistener 50 inside which is injected steam as shown by arrow 51, for form a steam-saturated air stream which is then fed directly to said zone 19 through the above-mentioned outlet opening 33.

The amount of air fed through pipe 32 into zone 19 corresponds for example to 10% from the total amount of air flowing.

Thus when the air flow rate to blowing manifold 1 is in the range from 40 to 50 m³/hour, the flow rate of air subjected to conditioning and passing through outlet opening 33 is in the range of 5 m³/hour.

It would possibly be possible to provide an additional micro-filter 34' connected in parallel with micro-filter 34. This would allow passing the gas to be sterilized alternately through one of said micro-filters while the other one is treated with microwaves for a sufficiently long time to insure destroying the micro-organisms retained therein.

The air flow in the circuit of the sterilizing apparatus is insured by one or a plurality of pumps or blowers 52, of blowing or high-pressure type.

Figure 7:
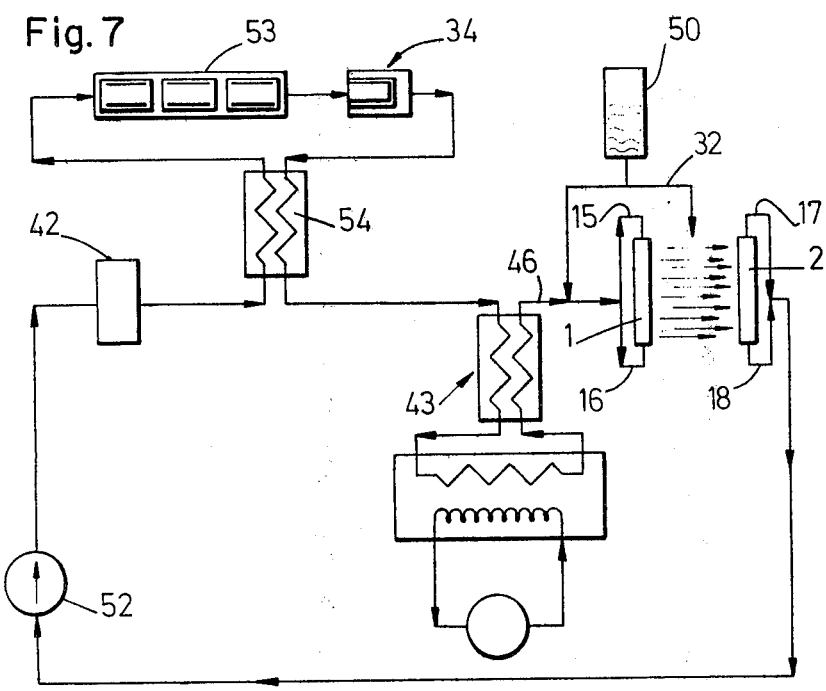
FIG. 7 is a block diagram of a sterilizing apparatus in a second embodiment.

The embodiment of the invention as shown in FIG. 7 differs essentially relative to the embodiment shown in FIGS. 5 and 6 by the sterilizing means used to destroy the micro-organisms in the filtering medium 37.

In said embodiment, sterilizing is performed with infra-red radiation. In this respect the micro-filter is preceded by a heating chamber 53 allowing to heat the gases to a temperature from 180° to 220° C. Thus the filtering medium 34 is indirectly brought to the sterilizing temperature by the gas stream.

Said chamber 53 is preceded by a heat exchanger 54 operating by recovery and used to pre-heat the gas stream for instance to a temperature of about 100° C. before entering chamber 53, by means of that stream having passed through micro-filter 34. Said gas is thereafter cooled in cooling unit 43 which should however have a much larger capacity then cooler 43 as shown in FIG. 5.

Indeed in the embodiment as shown in FIGS. 5 and 6, the filtering medium 37 is heated inwardly due to a friction action on a molecular and atomic scale in the dielectric from the filtering medium under the action of the electro-magnetic field generated by said microwaves. As the air molecules are not subjected to said friction action, the air will undergo but a slight temperature increase as already mentioned above, during the passage thereof for a very short time through the filtering medium.

This does comprise one of the reasons for the marked preference given to the use of microwaves for sterilizing the air. The wave frequency lies between 2,000 and 30,000 Mhz. and preferably in the range of 2,450 MHz. for which very efficient bactericidal results have been noticed.

In some cases however a sterilizing by microwaves might be combined with a sterilizing by infra-red radiation.

By adapting the structure and the flow rate of the air to be sterilized in the apparatus, it is possible to use same advantageously to retain inside an enclosure such as a room or part of a room, a sterile and perfectly conditioned atmosphere. This may mostly be useful for patients who are very sensitive to infections, such as patients having burns over a large portion of the body, etc.

For such an application, the installation has blowing nozzles for the air orginating from the sterilizing and sucking nozzles mounted inside the enclosure concerned to allow re-cycling air therefrom to said sterilizing apparatus.

Another application lies in combining the sterilizing apparatus with an apparatus for air-conditioning in a building. In such a case, it is advantageously possible to mount the micro-filter inside a conventional air-conditioning shaft.

The sterilizing apparatus can be controlled by means of a microprocessor.

On the other hand in some cases, it would be possible to condition in the same as the air fed through pipe 32 into zone 19, part or even all of that air used to form curtain 3.

I claim:

1. A method of conditioning and protecting a particular part of a preselected zone, said part being one in which a manipulation is to be effected, against contaminating agents entering from the outside environment, said method comprising:
providing a substantially laminar stream of an essentially sterile gas which has an upstream end and a downstream end, said laminar stream forming a gas curtain that defines one boundary side of the preselected zone;
delivering into said particular part of said zone a substantially continuous flow of an essentially sterile conditioned gas, said flow being adjacent the boundary of said zone remote from said gas curtain and in a direction opposite to that of said laminar gas stream and being at a preselected speed adjusted relative to the speed of the laminar gas stream;
and deflecting said flow arcuately toward the upstream end of said laminar stream to produce an interaction between said flow and said stream which directs said flow along said stream toward the downstream end and thus controls intrusion of said laminar stream into said zone and generates above said part of said zone a very slow, substantially stable circulation of gas which is continuously renewed at a low speed by said flow of sterile conditioned gas and by an exchange between gas from the flow and gas from the laminar stream.

2. The method of claim 1 which includes the steps of positioning a surface at which a manipulation is to be effected so it forms a boundary of said particular part of said zone which is remote from said gas curtain, and sealing all sides of said surface with solid curtains that extend upwardly to the plane of said gas curtain.

3. The method of claim 1 or 2 in which the distance from said flow of sterile conditioned gas to said gas curtain is in a range from about 10 cm to 30 cm.

4. The method of claim 3 in which the gas curtain is formed by blowing gas into the upstream end at a slow speed and generating suction at the downstream end.

5. The method of claim 4 in which the suction gas flow rate is larger than the blown gas flow rate.

6. The method of claim 3 in which the flow of sterile conditioned gas is moistened to a controlled level of humidity.

7. The method of claim 3 in which the gas curtain is given a stream speed in the range of about 2 m/sec. to about 20 m/sec.

8. The method of claim 3 in which the gas curtain is given a mean thickness in the range of about 0.2 cm to 5 cm.

9. The method of claim 3 in which the distance from the upstream end to the downstream end of the gas curtain is in the range of about 40 cm to about 70 cm, and the width of said gas curtain is in the range of about 20 cm to 60 cm.

* * * * *